(12) United States Patent
Rada et al.

(10) Patent No.: US 9,272,127 B2
(45) Date of Patent: Mar. 1, 2016

(54) CONNECTOR FOR A FLUID TRANSPORT LINE OF A MEDICAL DEVICE

(75) Inventors: Hiram Rada, Lyons (FR); Nicolas Semenzato, Decines Charpieu (FR)

(73) Assignee: Gambro Industries SAS, Meyzieu Cedex (FR)

( * ) Notice: Subject to any disclaimer, the term of this patent is extended or adjusted under 35 U.S.C. 154(b) by 413 days.

(21) Appl. No.: 13/640,980

(22) PCT Filed: Apr. 6, 2011

(86) PCT No.: PCT/IB2011/000747
§ 371 (c)(1),
(2), (4) Date: Jan. 23, 2013

(87) PCT Pub. No.: WO2011/128748
PCT Pub. Date: Oct. 20, 2011

(65) Prior Publication Data
US 2013/0116629 A1    May 9, 2013

(30) Foreign Application Priority Data
Apr. 13, 2010   (EP) ..................................... 10003885

(51) Int. Cl.
*F16K 11/07* (2006.01)
*A61M 39/10* (2006.01)
(Continued)

(52) U.S. Cl.
CPC ............. *A61M 39/10* (2013.01); *A61M 39/105* (2013.01); *A61M 39/223* (2013.01); *A61M 39/225* (2013.01); *A61M 39/26* (2013.01);
(Continued)

(58) Field of Classification Search
CPC .. F16L 37/40; F16L 37/46; Y10T 137/86879; Y10T 137/87941

USPC .................. 137/268, 614.02, 614.03, 614.06, 137/614.05, 625.48, 637.05, 862, 871; 251/149, 149.1, 149.6, 149.7, 149.9; 604/85; 141/293, 302, 347
See application file for complete search history.

(56) References Cited

U.S. PATENT DOCUMENTS 3,399,776 A * 9/1968 Knuth ............................ 210/234
3,476,137 A * 11/1969 Eisendrath .................... 137/268
(Continued)

FOREIGN PATENT DOCUMENTS

AU           199870078        1/1999
EP           0 070 087        1/1983
(Continued)

*Primary Examiner* — R. K. Arundale
(74) *Attorney, Agent, or Firm* — K&L Gates LLP (57) ABSTRACT

Connector for a fluid transport line of a medical device, comprising: a first body having a first access port for a fluid, a second access port for a fluid, and a first fluid path extending in the first body and directly connecting, for fluid transport, the first access port and second access port, at least a second body, mountable to the first body, having at least a third access port for a fluid, the second body being movable with respect to the first body at least between: a main operating position in which the first fluid path is interrupted and in which a second fluid path is defined and enabled, for fluid transport, from the first access port to the third access port, and an auxiliary operating position in which the first fluid path is enabled and in which the second fluid path is interrupted. The second body has at least a fourth access port for a fluid and in the main operating position a third fluid path is defined and enabled, for fluid transport, from the second access port to the fourth access port, the third fluid path being interrupted in the auxiliary operating position.

17 Claims, 6 Drawing Sheets

(51) Int. Cl.
*A61M 39/22* (2006.01)
*A61M 39/26* (2006.01)
*A61M 39/28* (2006.01)

(52) U.S. Cl.
CPC ........ *A61M 39/28* (2013.01); *Y10T 137/86879* (2015.04); *Y10T 137/87941* (2015.04)

(56) References Cited

U.S. PATENT DOCUMENTS

| | | | |
|---|---|---|---|
| 4,048,996 | A | 9/1977 | Mittleman et al. |
| 4,533,348 | A * | 8/1985 | Wolfe et al. .................... 604/85 |
| 4,541,829 | A | 9/1985 | Munsch et al. |
| 4,701,159 | A | 10/1987 | Brown et al. |
| 4,874,366 | A * | 10/1989 | Zdeb et al. .................... 604/518 |
| 5,540,653 | A | 7/1996 | Schock et al. |
| 5,769,385 | A | 6/1998 | Burrous et al. |
| 5,771,914 | A | 6/1998 | Ling et al. |
| 6,177,049 | B1 | 1/2001 | Schnell et al. |
| 6,308,737 | B1 | 10/2001 | Krivitski |
| 6,319,465 | B1 | 11/2001 | Schnell et al. |
| 6,695,807 | B2 | 2/2004 | Bell et al. |
| 6,871,878 | B2 | 3/2005 | Miros |
| 6,913,056 | B2 | 7/2005 | Landherr et al. |
| 6,971,680 | B2 | 12/2005 | Nakanishi et al. |
| 7,727,465 | B2 * | 6/2010 | Papageorge .................... 422/37 |
| 2001/0031222 | A1 | 10/2001 | Schnell et al. |
| 2003/0070273 | A1 | 4/2003 | Kust |
| 2005/0038413 | A1 | 2/2005 | Sansoucy |
| 2005/0131335 | A1 | 6/2005 | Drott et al. |
| 2005/0173056 | A1 | 8/2005 | Landherr et al. |
| 2007/0113892 | A1 * | 5/2007 | Chiriac et al. ............. 137/205.5 |
| 2008/0147012 | A1 | 6/2008 | Rome |

FOREIGN PATENT DOCUMENTS

| | | |
|---|---|---|
| EP | 0 238 750 | 9/1987 |
| EP | 0 704 227 | 4/1996 |
| EP | 0 966 981 | 12/1999 |
| EP | 1 024 854 | 8/2000 |
| FR | 2 459 663 | 1/1981 |
| WO | 81/02980 | 10/1981 |
| WO | 83/04373 | 12/1983 |
| WO | 84/00340 | 2/1984 |
| WO | 88/06895 | 9/1988 |
| WO | 00/24440 | 5/2000 |
| WO | 01/10485 | 2/2001 |
| WO | 2004/037339 | 5/2004 |
| WO | 2006/043883 | 4/2006 |
| WO | 2009/001152 | 12/2008 |

* cited by examiner

CONNECTOR FOR A FLUID TRANSPORT LINE OF A MEDICAL DEVICE

TECHNICAL FIELD

The present invention relates to a connector for a fluid transport line of a medical device. The medical device can be for example a machine for extracorporeal blood treatment or for treatment of renal insufficiency or for receiving and storing liquid from a donor. The liquid can be treatment liquid or can be liquid taken from a patient or donor. The invention is especially useful, but not only, when applied to connect a main fluid line with an auxiliary fluid line that has to be selectively put in fluid communication with the main fluid line or excluded from liquid communication with the same, particularly in medical devices such as dialysis machines or similar.

BACKGROUND

As it is known in the art, patients suffering from kidney failure or renal insufficiency, or patients suffering of particular pathologies should be submitted to specific treatments. More in detail, it is known to treat blood in an extracorporeal circuit in order to carry out ultrafiltration, haemodialysis, haemofiltration, haemodiafiltration, plasmapheresis, blood component separation, blood oxygenation, etc. . . .

Extracorporeal blood treatment means taking the blood from a patient, treating the blood outside the patient, and returning the treated blood to the patient. Normally, blood is removed from a blood vessel, sent into a withdrawal line of an extracorporeal circuit, passed through a blood-treating unit and returned to another or to the same blood vessel. Extracorporeal blood treatment is typically used to extract undesirable matter or molecules from the patient's blood, and/or to add beneficial matter or molecules to the blood. Extracorporeal blood treatment is used with patients incapable of effectively eliminating matter from their blood, for example in the case of a patient who is suffering from temporary or permanent kidney failure. These and other patients may undergo extracorporeal blood treatment to add to or to eliminate matter from their blood, to maintain an acid-base balance or to eliminate excess body fluids, for instance. Extracorporeal blood treatment is typically performed by sampling the patient's blood in a continuous flow, by introducing the blood into a primary chamber of a filter in which the blood comes into contact with a semi-permeable membrane. The semi-permeable membrane selectively lets the unwanted matter contained in the blood pass through the membrane, from the primary chamber to the secondary chamber, and also selectively lets the beneficial matter contained in the liquid going into the secondary chamber pass through the membrane to the blood going into the primary chamber, according to the type of treatment. A number of extracorporeal blood treatments can be performed by the same machine, also by selectively activating or excluding certain parts of the circuit. In ultrafiltration (UF) treatment, the unwanted matter is eliminated from the blood by convection through the membrane in the secondary chamber. In haemofiltration (HF) treatment, the blood runs through the semipermeable membrane as in UF, and the beneficial matter is added to the blood, typically by the introduction of a fluid into the blood, either before, or after its passage through the filter and before it is returned to the patient. In haemodialysis (HD) treatment, a secondary fluid containing the beneficial matter is introduced into the filter's secondary chamber. The blood's unwanted matter crosses the semi-permeable membrane and penetrates into the secondary fluid, and the beneficial matter of the secondary fluid can cross the membrane and penetrate into the blood. In haemodiafiltration (HOF) treatment, the blood and the secondary fluid exchange their matter as in HO, and further, matter is added to the blood, typically by introducing a fluid into the treated blood before it is returned to the patient as in HF, and the unwanted matter is also eliminated from the blood by convection. In each treatment, the secondary fluid goes through the filter's secondary chamber and receives the blood's unwanted matter by means of the membrane. This liquid is then extracted from the filter: it is commonly called waste, and is sent to a drain or to a receptacle then intended to be discharged into a drain. In fluid transport lines of medical devices, pumps are usually used in order to pump different fluids, such as blood, treatment liquids, waste liquids, along the transport lines.

In known fluid transport lines of medical devices, different parts of the circuit are usually connected by conventional connectors, for example luer lock type connectors. Known connectors are provided to firmly lock together different fluid transport lines to allow fluid passage between them. As already stated, in known medical devices it is sometimes needed to selectively exclude from the circuit a certain part of the circuit or specific element that is not necessary for a particular treatment. It is also sometimes needed to remove or substitute an element of the circuit, for example to replace an exhausted device. In order to carry out the above indicated operations, a first known solution consists in stopping the functioning of the whole medical device in order to carry out the needed operation, i.e. changing the connections of the circuit in order to exclude the elements not needed or removing or replacing some elements from the circuit. An alternative solution consists in using specific by-pass valves that can be selectively activated in order to deviate the liquid flow from a certain part of the circuit, thus allowing to exclude such part of the circuit and consequently to continue the treatment without the excluded element or to remove or substitute the excluded element from the circuit. When a certain part of the circuit is excluded by the bypass valve, the element to be substituted is disconnected from the remaining part of the circuit by disconnecting the luer type connectors or other connectors used.

The known devices have the following problems. It is to be noted that the first known solution consisting in stopping the medical device in order to remove or substitute an element located in a certain part of the circuit is quite disadvantageous, since it causes a relevant waste of time, in particular when the required operations have to be carried out during a treatment and between two different treatments. Furthermore such first solution requires always a removal of a certain part of the circuit from the remaining circuit in order to exclude such part from the treatment, thereby causing further waste of time for disconnecting such part when not needed and for subsequently connecting again such part when needed again. These operations have to be carried out manually, further involving the risk of making mistakes in the connections and of damaging some parts of the circuits and in particular the connectors.

The second solution above described, in which a by-pass valve is used to exclude a certain part of the circuit when not needed, overcomes some of the problems of the first solution, since it does not require to stop the circuit and to disconnect and then to connect again certain parts of the circuit when such parts are not needed for a certain treatment and then needed again. Also such second solution anyway has some drawbacks, since the known by-pass valves usually have a complicated structure and are not easy to actuate. Furthermore such by-pass valves do not allow to automatically disconnect the by-passed part of the circuit in order to remove or substitute a part of the circuit from the medical device, but allow only to bypass the desired part of the circuit, which has to be subsequently removed from the rest of the circuit with further connectors.

SUMMARY

It is one object of the present invention in one of his aspects to overcome some of the limits of the known art. A further object of the invention in one of his aspects is providing a connector for a fluid transport line of a medical device that allows to selectively exclude a part of a fluid flow circuit from the remaining part of the circuit. It is a further object of the invention in one of his aspects providing a connector for a fluid transport line of a medical device that has a simple and robust structure. It is a further object of the invention in one of his aspects providing a connector for a fluid transport line of a medical device that can be easily and quickly actuated to bypass a certain part of the circuit. Another object of the invention in one of his aspects is providing a connector for a fluid transport line of a medical device that allows to automatically exclude and disconnect a certain part of the circuit or a particular device from the rest of the circuit, also by automatically removing it from the circuit. It is then an auxiliary aim of the invention in one of his aspects to provide a connector for a fluid transport line of a medical device of different structure and conception as compared with the corresponding devices of the prior art, and which is cheap and reliable. Other advantages and characteristics of the invention will become clear from reading the following description. One or more of the foregoing aims are substantially achieved by a connector for a fluid transport line of a medical device according to one or more of the appended claims.

The present invention is described with particular reference to connector applied to an extracorporeal blood treatment circuit without thereby limiting the scope of the invention to this specific application. The connector may be applied to different kind of fluid transport lines. The present invention relates to a connector for a fluid transport line of a medical device, according to the enclosed connector independent claims or to any of the dependent connector claims, in any combination between them. The invention further relates, in one of its aspects, to a connector according to any of the enclosed connector claims, in which, in the main operating position, the second body is mounted to said first body.

The invention further relates, in one of its aspects, to a connector according to any of the enclosed connector claims, in which, in the main operating position, the second body is directly mounted to said first body. The invention further relates, in one of its aspects, to a connector according to any of the enclosed connector claims, in which, in the main operating position, the second body is into contact with said first body.

The invention further relates, in one of its aspects, to a connector according to any of the enclosed connector claims, in which a second body is permanently mounted to a first body and/or in which a second body is mounted to a first body both in a main position and in an auxiliary operating position. The invention further relates, in one of its aspects, to a connector according to any of the enclosed connector claims, in which the second body may be made in one piece with the first body. The invention further relates, in one of its aspects, to a connector according to any of the enclosed connector claims, in which the second body is mounted to the first body either in the main operating position or in the auxiliary operating position. The invention further relates, in one of its aspects, to a connector according to any of the enclosed connector claims, in which the second body is directly mounted to the first body either in the main operating position or in the auxiliary operating position. The invention further relates, in one of its aspects, to a connector according to any of the enclosed connector claims, in which the second body is into contact with the first body either in the main operating position or in the auxiliary operating position. The invention further relates, in one of its aspects, to a connector according to any of the enclosed connector claims, in which the second body is mounted to the first body in the main operating position. The invention further relates, in one of its aspects, to a connector according to any of the enclosed connector claims, in which the second body is mounted to the first body in the auxiliary operating position. The invention further relates, in one of its aspects, to a connector according to any of the enclosed connector claims, in which the second body is directly mounted to the first body in the main operating position. The invention further relates, in one of its aspects, to a connector according to any of the enclosed connector claims, in which the second body is directly mounted to the first body in the auxiliary operating position. The invention further relates, in one of its aspects, to a connector according to any of the enclosed connector claims, in which the second body is into contact with the first body in the main operating position. The invention further relates, in one of its aspects, to a connector according to any of the enclosed connector claims, in which the second body is into contact with the first body in the auxiliary operating position. The invention further relates, in one of its aspects, to a connector according to any of the enclosed connector claims, in which the second body is a part of the first body. The invention further relates, in one of its aspects, to a connector according to any of the enclosed connector claims, in which a portion of a third path is further defined in a second part of the first body, and in which in the second position also the third path is enabled. The invention further relates, in one of its aspects, to a connector according to any of the enclosed connector claims, in which the first body further comprises a third part in which a portion of the first path and a portion of the third path are defined, the third part being also movable with respect to the first part between a first position, corresponding to the auxiliary operating position, in which the first path is enabled, and a second position, corresponding to the main operating position, in which the first path is interrupted and the third path is enabled. The invention further relates, in one of its aspects, to a connector according to any of the enclosed connector claims, in which the second body is mounted to the second part and/or the third part of the first body in the main position and is detached from the second part and/or the third part in the auxiliary position. The invention further relates, in one of its aspects, to a connector according to any of the enclosed connector claims, in which the first, second and/or third path are respectively enabled by aligning the portions of the first, second and/or third path defined in the second part and/or third part with corresponding portions of fluid path defined in the first part of the first body. The invention further relates, in one of its aspects, to a connector according to any of the enclosed connector claims, in which the second body is adapted to move the second part and/or the third part of the first body between the first and second position, or viceversa, when the second body is mounted or dismounted from the first body. The invention further relates, in one of its aspects, to a connector according to any of the enclosed connector claims, in which at least the second part and/or the third part is mounted to the first body by an elastic element configured for maintaining the second part and/or the third part in the first position or in the second position. The invention further relates, in one of its aspects, to a connector according to any of the enclosed connector claims, in which the second part and/or the third part are shiftably movable between the first and the second positions. The invention further relates, in one of its aspects, to a connector according to any of the enclosed connector claims, in which the second body is shiftably mountable to the second part and/or third part of the first body. The invention further relates, in one of its aspects, to a connector according to any of the enclosed connector claims, in which the second body further comprises a fifth access port for a fluid and a sixth access port for a fluid, the fifth and sixth access port being respectively directly connected, for fluid transport, to the third and fourth access ports respectively by a fourth and by a fifth fluid paths. The invention further relates, in one of its aspects, to a connector according to any of the enclosed connector claims, in which the second body is rotatable with respect to the first part of the first body to move from the main operating position to the auxiliary operating position. The invention further relates, in one of its aspects, to a connector according to any of the enclosed connector claims, comprising a plurality of pushing elements. The invention further relates, in one of its aspects, to a connector according to any of the enclosed connector claims, in which the pushing elements comprise protrusions of the first and/or second body adapted to press at least one of tubes in the main operating position. The invention further relates, in one of its aspects, to a connector according to any of the enclosed connector claims, in which the pushing elements are movably mounted in the first and/or second body through elastic elements, to push at least one of the tubes to interrupt fluid passage in the auxiliary operating position or in the main operating position, the pushing elements being movable to enable fluid passage in the at least one of the tubes in a respective opposite operating position corresponding to the main or auxiliary operating position. The invention further relates, in one of its aspects, to a connector according to any of the enclosed connector claims, in which the pushing elements comprise a flexible elongated element hingedly mounted in the first body and/or in the second body, the elongated element having at least a first protrusion adapted to press a first corresponding tube to prevent fluid passage and at least a second protrusion adapted to enable fluid passage in a second corresponding tube, in the auxiliary position, the first protrusion being adapted to enable fluid passage in the first corresponding tube and the second protrusion being adapted to press the second corresponding tube to prevent fluid passage, in the main position. The invention further relates, in one of its aspects, to a connector according to any of the enclosed connector claims, in which the flexible elongated element has at least a third protrusion adapted to press a third corresponding tube to prevent fluid passage in the auxiliary position, the third protrusion being adapted to enable fluid passage in the third corresponding tube in the main position. The invention further relates, in one of its aspects, to a connector according to any of the enclosed connector claims, in which the flexible elongated element is disposed in the first body and is moved in the main position by a respective pushing element of the second body, and/or viceversa. The invention further relates, in one of its aspects, to a fluid transport line comprising a connector according to any of the enclosed connector claims. The invention further relates, in one of its aspects, to a fluid transport line for a medical device according to any of the enclosed claims comprising a main fluid line, an auxiliary fluid line and a connector for a fluid transport line of a medical device comprising at least a body having: a first access port for a fluid, connected to a first access port, of the main fluid line, a second access port for a fluid, connected to a second access port of the main fluid line, a first fluid path extending in the first body and directly connecting, for fluid transport, the first access port and second access port, a third access port for a fluid, operatively connected to a first access port of the auxiliary fluid line, a second fluid path defined for fluid transport from the first access port to the third access port, the connector defining a main operating position in which the first fluid path is interrupted and in which the second fluid path is enabled, for fluid transport, from the first access port to the third access port, and an auxiliary operating position in which the first fluid path is enabled and in which the second fluid path is interrupted, the auxiliary fluid line being bypassed by the connector in the auxiliary operating position. The invention further relates, in one of its aspects, to a fluid transport line according to any of the enclosed claims, in which the connector further defines a sixth fluid path for directly connecting the third access port and the fourth access port for fluid transport, the sixth fluid path being enabled in the auxiliary position and being interrupted in the main position. The invention further relates, in one of its aspects, to a fluid transport line according to any of the enclosed fluid transport line claims, comprising a connector according to any of the enclosed connector claims and in which the first access port and the second access port are provided on a first body of the connector and in which the third access port is provided on a second body of the connector, movable with respect to the first body. The invention further relates, in one of its aspects, to a fluid transport line according to any of the enclosed fluid transport line claims, in which the connector is according to any of attached connector claims and in which the main operating position and the auxiliary operating position are defined by relative positions of the first and the second bodies of the connector. The invention further relates, in one of its aspects, to a medical device according to any of the enclosed device claims, in which the main fluid line is a main part of a circuit for extra-corporeal blood circulation and in which the auxiliary line is an auxiliary part of the circuit for extracorporeal blood circulation, the auxiliary part of the circuit for extra-corporeal blood circulation being selectively connected to the main fluid line when the connector is in the main operating position and bypassed when the connector is in the auxiliary operating position. The invention further relates, in one of its aspects, to a medical device comprising a connector according to any of the enclosed connector claims. The invention further relates, in one of its aspects, to a method for automatically establishing and interrupting a fluid communication between a main fluid line and an auxiliary fluid line of a fluid transport line for a medical device, comprising the steps of selectively configuring a connector, having a first and a second access ports for a fluid connected respectively to a first and a second access port of the main fluid line and at least a third access port for a fluid operatively connected to a first access port of the auxiliary fluid line, between a main position in which a first fluid path, defined in the connector for directly connecting, for fluid transport, the first access port and second access port, is interrupted and in which a second fluid path from the first access port to the third access port is enabled, and an auxiliary position in which the first fluid path is enabled and in which the second fluid path is interrupted, the auxiliary fluid line being bypassed by the connector in the auxiliary operating position. The invention further relates, in one of its aspects, to a method for automatically connecting and disconnecting a main fluid line and an auxiliary fluid line of a fluid transport line for a medical device, comprising the steps of selectively configuring a connector, having a first body with a first and a second access ports for a fluid connected respectively to a first and a second access port of the main fluid line and a second body with a third and a fourth access ports for a fluid operatively connected respectively to a first and a second access ports of the auxiliary fluid line, between a main position in which the second body is mounted to the first body and in which a first fluid path, defined in the connector for directly connecting, for fluid transport, the first access port and second access port, is interrupted and in which a second fluid path from the first access port to the third access port and a third fluid path from the second access port to the fourth access port are enabled, and an auxiliary position in which in which the second body is separated from the first body, the first fluid path is enabled and in which the second and third fluid paths are interrupted, the auxiliary fluid line being bypassed and separated from the main fluid line in the auxiliary operating position.

BRIEF DESCRIPTION OF THE DRAWINGS

Additional characteristics and advantages of the present invention will appear with the detailed description of not exclusive embodiments of a connector for a fluid transport line of a medical device according to the invention. This description will be given below with reference to the annexed drawings, which are supplied for information purposes and are thus not limiting.

DETAILED DESCRIPTION

Figure 1:
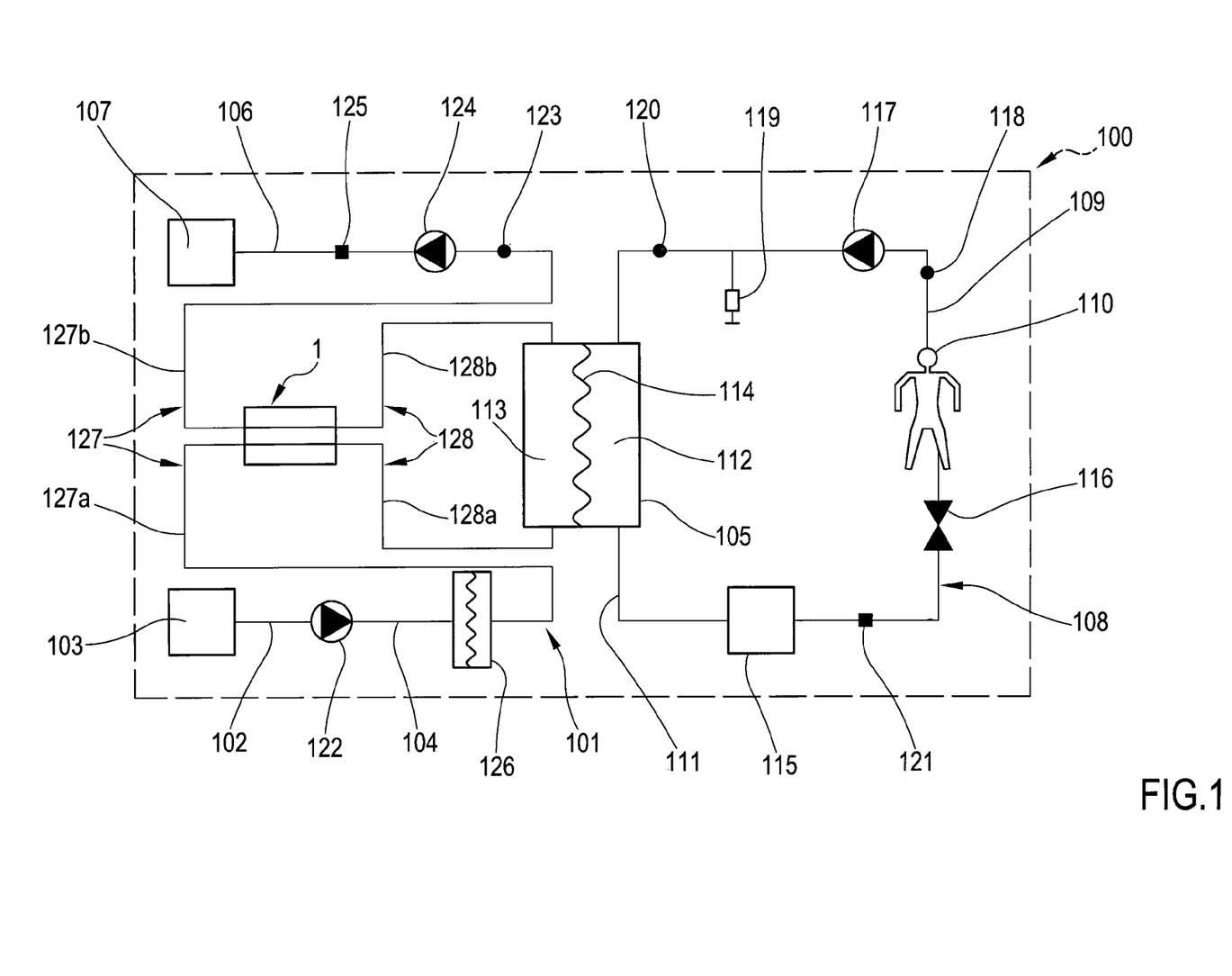
FIG. 1, represents an example of a fluid flow circuit of a medical device, including a connector according to an illustrating embodiment of the present invention, in a main operating position.
Figure 2:
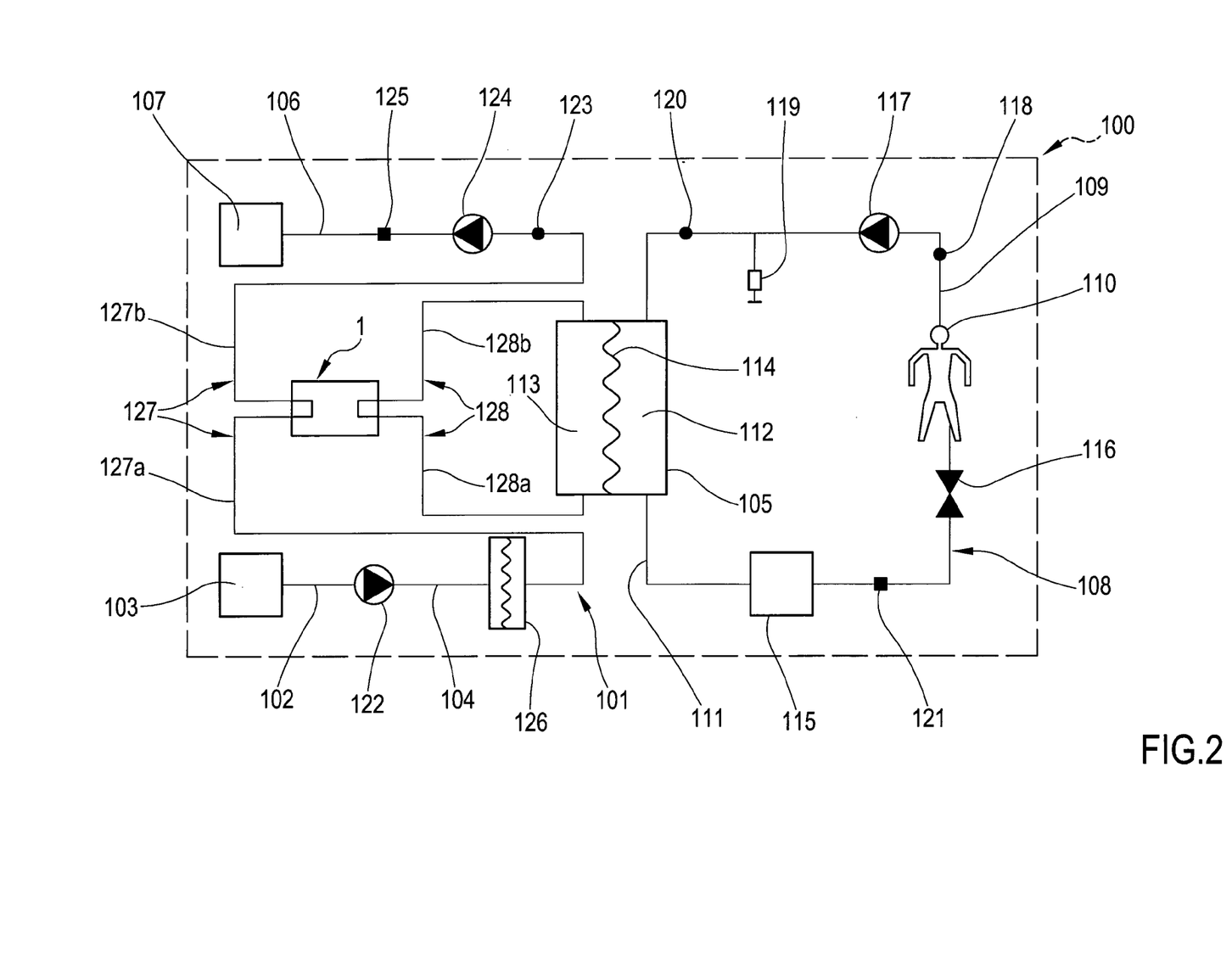
FIG. 2 represents the fluid flow circuit of FIG. 1 with the connector in an auxiliary operating position.
Figure 3:
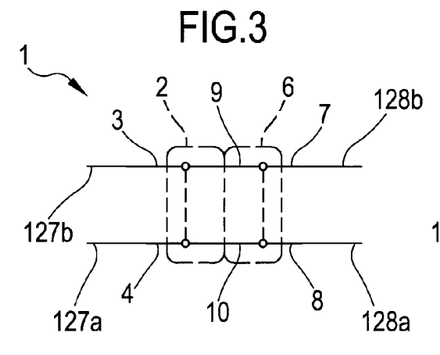
FIG. 3 represents a view of a schematic representation of a connector according to an aspect of the present invention in a main operating position.
Figure 4:
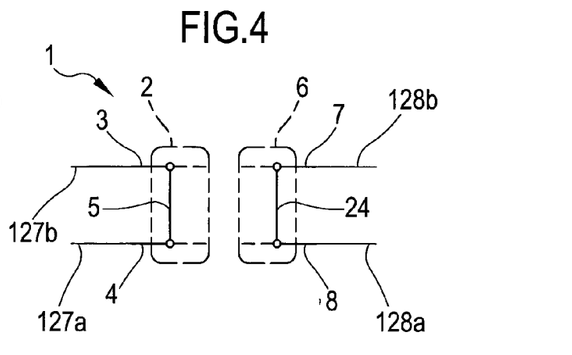
FIG. 4 is a view corresponding to FIG. 3 in an auxiliary operating position.
Figure 5:
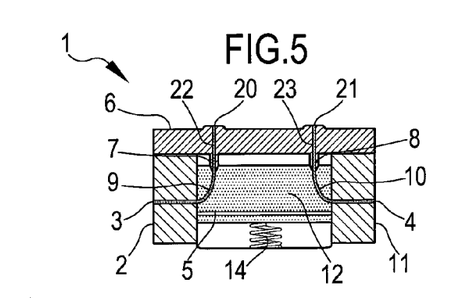
FIG. 5 shows a sectioned view of the first embodiment of the connector according to the present invention in a main operating position.
Figure 13:
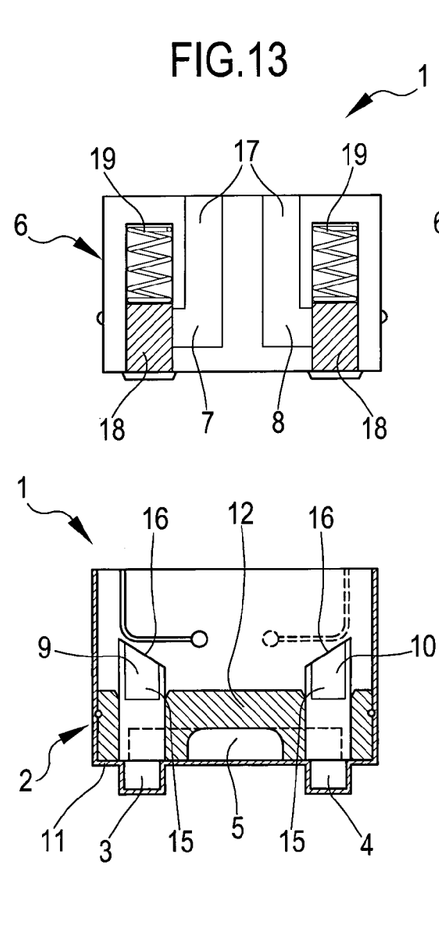
FIG. 13 shows a sectioned lateral view of a fifth embodiment of a connector according to the present invention in an auxiliary operating position.
Figure 14:
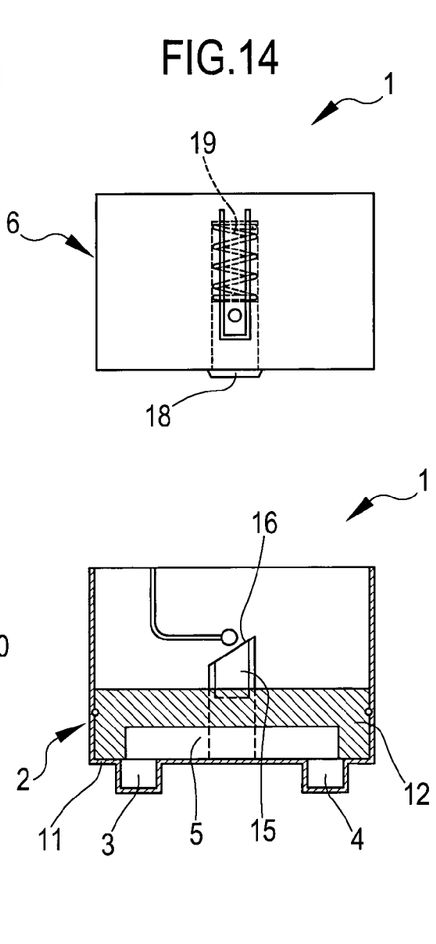
FIG. 14 shows a view of the connector of FIG. 13 in an intermediate main operating position.
Figure 15:
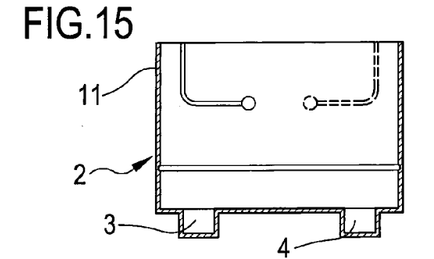
FIG. 15 is a sectioned lateral view of a first part of a first body of the connector of FIG. 13.
Figure 15A:
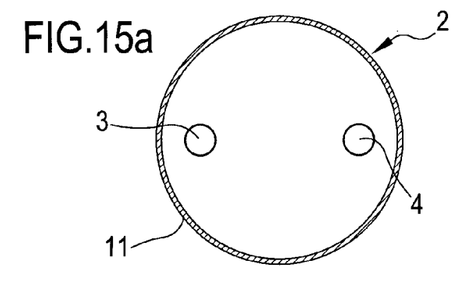
FIGS. 15a and 15b show respectively a view from above and a view from below of the first part of FIG. 15.
Figure 15B:
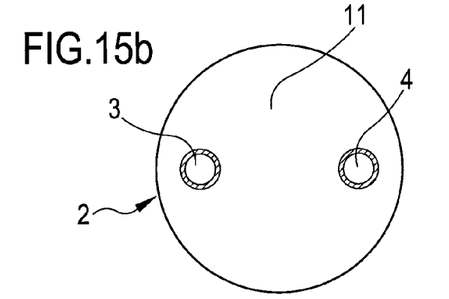
Figures 16, 17:
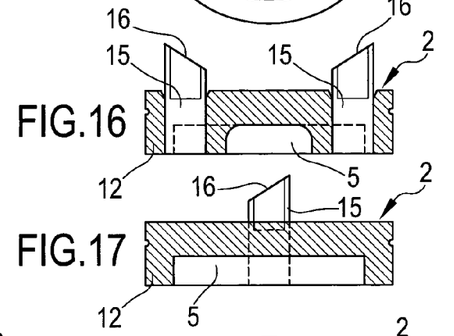
FIG. 16 is a sectioned lateral view of a second part of a first body of the connector of FIG. 13.
FIG. 17 is a sectioned lateral view of the second part of the first body of the connector of FIG. 15, in a second operating position rotated by 90° around a central axis parallel to the sheet, with respect to the position of FIG. 15.
Figure 16A:
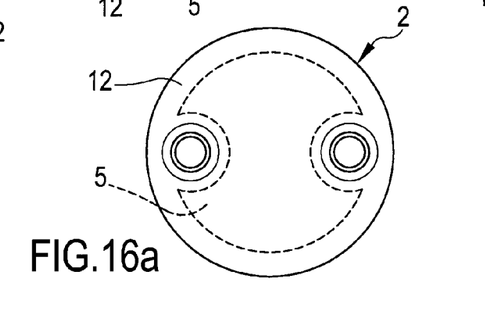
FIGS. 16a and 16b show respectively a view from above and a view from below of the second part of FIG. 16.
Figure 16B:
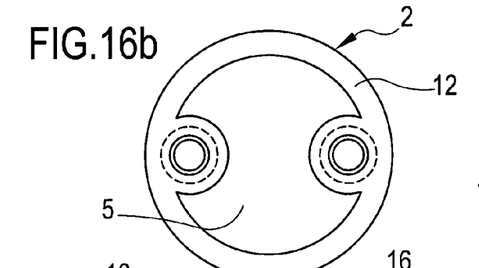

With reference to the cited figures, 100 denotes a fluid flow circuit of a medical machine for fluid treatment. The machine can be, for example, a machine for blood treatment, such as a machine for treatment of kidney failure (for example a hemo (dia)filtration machine or a hemodialysis machine, for chronic or intensive therapy) or liver insufficiency or a plasmapheresis machine or any other type of medical machine suitable for treatment of a fluid. In the following description, reference will be made to a machine for extracorporeal treatment of blood in its essential components of known type and only partially mentioned. An example of a realization of a fluid flow circuit 100 is schematically illustrated in FIGS. 1 and 2. It is to be noted that the specific structure of the fluid flow circuit 100 is not relevant to the ends of the present invention and that therefore the invention can be applied to many other fluid flow circuits which are different from the one specifically shown in FIGS. 1 and 2, according to the functional and design requirements of each single medical apparatus. In the example shown in the figures, the fluid flow circuit 100 comprises an hydraulic circuit 101 that exhibits at least a supply channel 102, destined for transport of a treatment liquid from at least a source 103 towards a treatment station where one or more blood treatment unit 105 operate. The hydraulic circuit 101 further comprises at least a discharge channel 106 destined to transport a used liquid from the treatment unit 105 towards an evacuation zone, schematically denoted by 107 in FIGS. 1 and 2. It should be noted that the supply channel 101 is destined to cooperate with means for moving a fluid, such as at least a pump 122, for example a positive displacement pump, such as in particular a peristaltic pump, or a gear or diaphragm pump. In a variant, not illustrated since conventional in such a circuit, a branch may be provided downstream of the pump 122 and along the circulation direction, dividing the primary sterile fluid circuit into an inlet branch 104, leading to the blood treatment unit 105, and an infusion branch. In such variant the infusion branch may be connected to the blood removal line (arterial line)

and/or the blood return line (venous line) of the blood circuit to enable an infusion to be obtained directly into the blood (before and/or after the blood treatment unit 105) using sterile fluid. The inlet branch 104 brings the sterile fluid to the blood treatment unit 105 for exchange through the membrane 114. Obviously in the variant selector means (for example a valve element and/or means for moving, such as one or more pumps) will be present for determining the percentage quantities of fluid flow in the infusion branch and the inlet branch 104. The sterile fluid for dialysis thus enters the discharge channel 106 of the circuit and crosses a pressure sensor 123 provided for control of the functioning of the line. There are therefore further fluid movement means present, for example a drainage pump 124 which can control the flow in the discharge channel 106 of the circuit. The drainage pump 124 can, in general, be a positive displacement pump, such as for example a peristaltic pump, or a gear pump, or a diaphragm pump. The fluid to be eliminated thus crosses a blood leak detector 125 and is conveyed towards the evacuation zone 107. The treatment fluid (dialysis fluid or replacement fluid) can be purified before use by one or more ultrafilters 126. The fluid flow circuit 100 comprises also a blood circuit 108 which is also schematically represented in FIGS. 1 and 2 in its basic components. The specific structure of the blood circuit 108 is also not fundamental with reference to the present invention, and thus, with reference to FIGS. 1 and 2, a brief description of a possible embodiment of the circuit is provided, which should however be considered to be provided purely by way of non-limiting example. The blood circuit 108 comprises an arterial line 109 for removing blood from a vascular access 110 of a patient and a venous line 111 predisposed to return the treated blood to the vascular access. The blood circuit 108 of FIG. 2 further comprises a first chamber, or blood chamber 112, of the blood treatment unit 105 whose second chamber 113 is connected to the hydraulic circuit 100. In greater detail, the arterial line 109 is connected to the inlet of the blood chamber 112, while the venous line 111 is connected in outlet to the blood chamber 112. In turn, the supply channel 101 is connected in inlet to the second chamber 113, while the discharge channel 106 is connected in outlet to the second chamber. The blood treatment unit 105, for example a dialyser or an ultrafilter or a plasma filter or a hemofilter or a hemodiafilter, comprises, as mentioned, the two chambers 112 and 113, which are separated by a semi-permeable membrane 114, for example a hollow-fibre or plate-type membrane. A blood pressure sensor 118 is located on the arterial line 109 along the circulation direction of the blood from the removal zone (vascular access) towards the blood treatment unit 105. The arterial line 109 is further connected to a device for administering an anticoagulant 119, for example a syringe pump for providing appropriate anticoagulant doses (heparin). The arterial line can thus be provided, optionally, with a further pressure sensor 120 (arranged between a pump 117 and the unit 105) for surveying the correct flow internally of the blood circuit. The blood circuit can also comprise one or more air separators 115: the example of FIG. 2 shows a separator 115 on the venous line 111, upstream of a safety valve 116. The treated blood, exiting from the air separator device 115, crosses an air bubble sensor 121, provided to check for the absence of dangerous formations internally of the treated blood which must be returned into the patient's blood circuit. In particular, should the air bubble sensor 121 reveal the presence of faults in the blood flow, the machine, via the safety valve 116 (which might be a cock, a clamp or the like) it would be able immediately to block blood passage in order to prevent any type of consequence to the patient. The valve 116 can always be closed in the venous line should, for example for safety reasons, it become necessary to interrupt blood return to the vascular access 110. The means 3 for fluid treatment can also comprise one or more blood pump 117, for example positive displacement pumps such as peristaltic pumps; in the example of FIG. 2 there is a pump 117 on the arterial line 109. In general, the hydraulic circuit 100 is housed internally of a chamber in the machine body, while the blood circuit 108 is borne on a front panel of the machine body which also supports the peristaltic pump or pumps 117. The treatment unit 105 can be removable physically supported, by rapid-attachment means (of known type) arranged, for example, on a lateral wall of the machine structure itself. The treatment unit 105, in operating conditions of blood treatment, is connected both to the hydraulic circuit and to the blood circuit as already briefly mentioned. As is obvious and indeed known, means for fluid treatment comprise the cited sensors for detecting functioning parameters of the medical machine and also the cited actuators for intervening in order to modify the functioning parameters of the machine. Each medical machine in general comprises a control unit which is programmed at least to send command signals and to receive data from the means for fluid treatment. The control unit is thus active at least on the blood circuit and in particular on the pressure sensor 118, on the blood pump 117, on the heparin infusion device 119, on the further pressure sensor 120 as well as on the device for detecting the presence of air bubbles 121 and on the closing element 116. The control unit will be active on the pump 122, on any selector means present, on the pressure sensor 123, on the drainage pump 124 and will also receive information from the blood leak detector 125. Further, the control unit is set up to control the hydraulic circuit 100 of the sterile fluid and in particular will receive in input the data read off by any balances present on the machine relating to the weight of the various containers which may be in use on the machine. Obviously, apart from the control of the sensors and the actuators, the control unit may be predisposed to receive and control further sensors and actuators present on the machine in order to guarantee and monitor the functioning thereon. The machine for extracorporeal treatment may be provided with a fluid balance system, of the type used in a machine for hemodialysis and hemo(dia)filtration, for control of the patient's weight loss during the treatment, for example a flow-meter type, or a variable-volume volumetric chambers system, or a system including balances, or other systems of known type. The machine can be provided with a system, of known type, for on-line preparation of the treatment fluid (for example dialysis fluid and/or replacement fluid) starting from water and concentrates, and/or a system (of known type) for degassing and/or heating the fluids running through the system itself, and/or a purification system having one or more treatment fluid ultrafiltration stages. The control unit can, for example, comprise one or more digital microprocessing units or one or more units of an analog and/or digital type. The medical machine is provided with further standard components well know in the art and that will not mentioned or further described in the present description, such as for example a disinfection/cleaning system, a liquid loss sensor, a display, devices for entering data, and so on. According to the present invention, as shown in FIGS. 1 and 2, the fluid flow circuit 100 comprises at least a connector 1, that will be described in detail in the following description. In the example of the circuit shown a connector 1 is located in the hydraulic circuit 101 between the inlet branch 104 and the discharge channel 106, and in particular it is operatively interposed between a main fluid line 127 of the hydraulic circuit 101 (comprising both the inlet branch 104 and the discharge channel 106) and an auxiliary fluid line 128 (in which the blood treatment unit 105 is located). The connector 1 allows to selectively connect the auxiliary fluid line 128 (and the blood treatment unit 105) with the main fluid line 127, in particular by selectively connecting and disconnecting a first line 127a of the main fluid line 127 with a first line 128a of the auxiliary fluid line 128, and by selectively connecting and disconnecting a second line 127b of the main fluid line 127 with a second line 128b of the auxiliary fluid line 128. FIG. 1 shows a main operating position of the connector 1 in which the main fluid line 127 is in fluid communication with the auxiliary fluid line 128, and consequently the blood treatment unit 105 is operatively connected with the rest of the hydraulic circuit. FIG. 2 shows an auxiliary operating position of the connector 1 in which the main fluid line 127 is not in fluid communication with the auxiliary fluid line 128, and consequently the blood treatment unit 105 is excluded from the rest of the hydraulic circuit. In the auxiliary operating position of FIG. 2 the auxiliary fluid line 128 and the blood treatment unit 105 are bypassed and the fluid passes directly from the first line 127a to the second line 127b of the main fluid line 127. The connector could be applied to other parts of the circuit, in order to allow to bypass the further elements when not needed or to substitute such elements. In general terms, the main fluid line is a main part of a circuit for extra-corporeal blood circulation and the auxiliary line is an auxiliary part of the circuit for extra-corporeal blood circulation, the auxiliary part of the circuit for extra-corporeal blood circulation being selectively bypassable by the connector in the auxiliary operating position. The position of the connector 1 in the circuit is intended as an example and is not to be intended in any way limiting the present invention. It is to be noted that the connector 1 is represented schematically in FIG. 2 as a single element, even if in such auxiliary operating position the connector may also be made of two separate bodies, thereby automatically physically separating the main fluid line 127 and the auxiliary fluid line 128 in the auxiliary position, as will be clear from the following detailed description. In general terms, a connector 1 for a fluid transport line of a medical device comprises a first body 2 having a first access port 3 for a fluid, a second access port 4 for a fluid, and a first fluid path 5 extending in said first body 2 and directly connecting, for fluid transport, said first access port 3 and second access port 4. The connector 1 further comprises at least a second body 6, mountable to said first body 2, having at least a third access port 7 for a fluid and a fourth access port 8 for a fluid. The second body 6 is movable with respect to the first body 2 at least between a main operating position (shown for example in FIG. 3) in which the first fluid path 5 is interrupted and in which a second fluid path 9 is defined and enabled, for fluid transport, from the first access port 3 to the third access port 7, and in which a third fluid path 10 is defined and enabled, for fluid transport, from the second access port 4 to the fourth access port 8, and an auxiliary operating position (shown for example in FIG. 4) in which the first fluid path 5 is enabled and in which the second 9 and third 10 fluid paths are interrupted. The first access port 3 and the second access port 4 are provided in the first body 2 of the connector 1 and the third access port 7 and the fourth access port 8 are provided on a second body 6 of the connector 1, movable with respect to the first body 2. The main operating position and the auxiliary operating position are defined by relative positions of the first 2 and the second 6 body of the connector 1, since the second body 6 is movable between a plurality of operating positions. FIGS. 3 and 4 show respective operating positions of a schematic representation of a connector according to an aspect of the present invention. The schematic representation of FIGS. 3 and 4 corresponds for example to a third and a fourth embodiment of the invention (represented in FIGS. 9-12), that will be described in detail in the following description. According to such schematic representation and to the third and fourth embodiment shown in FIGS. 9-12, the second body 6 comprises a sixth fluid path 24 for directly connecting the third access port 7 and the fourth access port 8 for fluid transport. The sixth fluid path 24 is enabled in the auxiliary position and is interrupted in the main position. Different embodiments of a connector 1 according to the present invention will be described in further detail hereinafter. According to some peculiar embodiments of the invention (FIGS. 3-21), the second body 6 is removably mounted to the first body 2. In this case, the second body 6 can be detached from the first body 2 in the auxiliary operating position and is mounted to the first body 2 in the main position. According to the first, second and fifth embodiment (FIGS. 5-8 and 13-19), the first body 2 may comprise a first part 11 and at least a second part 12 in which a portion of the first path 5 and at least a portion of the second path 9 are defined. The second part 12 is movable with respect to the first part 11 between a first position (shown in FIGS. 6, 8, and 14), corresponding to the auxiliary operating position, in which the first path 5 is enabled, and a second position (shown in FIGS. 5, 7, and 13), corresponding to the main operating position, in which the first path 5 is interrupted and the second path 9 is enabled. In the first and fifth embodiment (FIGS. 5-6 and 13-19), a portion of the third path 10 is further defined in the second part 12, and in the second position also the third path 10 is enabled. In the second embodiment (FIGS. 7 and 8), the first body 2 further comprises a third part 13 in which a portion of the first path 5 and a portion of the third path 10 are defined. The third part 13 is also movable with respect to the first part 11 between a first position (shown in FIG. 8), corresponding to the auxiliary operating position, in which the first path 5 is enabled, and a second position (shown in FIG. 7), corresponding to the main operating position, in which the first path 5 is interrupted and the third path 10 is enabled. According to the second and the third embodiment of the invention (shown in FIGS. 5-8) the second body 6 is mounted to the second part 12 (and to the third part 13 in FIGS. 7-8) of the first body 2 in the main position and is detached from the second part 12 (and the third part 13) in the auxiliary position. In the first, second and fifth embodiments (FIGS. 5-8 and 13-14), the first 5, second 9 and/or third path 10 are respectively enabled by aligning respective portions of the first 5, second 9 and/or third path 10 defined in the second part 12 and/or third part 13 with corresponding portions of fluid path defined in the first part 11 of the first body 2. In the first and second embodiment (FIGS. 5-8) the second body 6 is adapted to move the second part 12 (and the third part 13) of the first body 2 between the first and second position, or viceversa, when the second body 6 is mounted or dismounted from the first body 2. At least the second part 12 (and the third part 13) is mounted to the first body 2 by an elastic element 14 configured for maintaining the second part 12 and/or the third part 13 in the first position or in the second position. In the second embodiment of FIGS. 7 and 8 two elastic elements 14 are provided, one for the second part and one for the third part of the first body 2. In the embodiments of FIGS. 5-8 the elastic element 14, for example a spring, is configured for maintaining the second 12 and third element 13 in the first position when the second body 6 is detached from the first part 11. In the embodiments of FIGS. 5-8, the second part 12 and/or the third part 13 are shiftably movable between the first and the second positions. In such embodiments, and also in the fifth embodiment of FIGS. 13-14, the second body 6 is shiftably mountable to the second part 12 and/or third part 13 of the first body 2. In the fifth embodiment of FIGS. 13-19, the second body 6 is rotatable with respect to the first part of the first body 2 to move from the main operating position to the auxiliary operating position. As shown in FIGS. 13-14, in the fifth embodiment the second part 12 is rotatably movable, with respect to the first part 11 of the first body 2, between the first and the second positions. In further detail, in the fifth embodiment starting from an auxiliary position shown in FIG. 14, in which the second body 6 is detached from the first body 2 and the first path 5 is enabled, the second body 6 can be firstly shifted to mount it to the second part 12 of the first body 2. In order to mount the second body 6 to the second part, two protruding portions 15, internally cave for allowing fluid transport and provided with an inclined upper edge 16, of the second part 12 enter into respective channels 17 of the second body 6 by moving two cursors 18, mounted in the channels 17 with elastic elements 19, in order to open an access to the same channels 17 and allow fluid passage from the second part 12 through the second body 6. Subsequently the second body 6 and the second part of the first body 2 are rotated together with respect to the first part 11 of the first body 2 to bring the connector 1 into the main position in which the first path 5 is interrupted and the second 9 and third path 10 are enabled. FIG. 13 shows a partially exploded view in which the second part 12 of the first body 2 is rotated by 90° with respect to the position of FIG. 14 so that the second 9 and third paths 10 are enabled, but in which the second body 6 is shown still separated from the first body 2 for clarity reasons. The main position corresponds to the position of FIG. 13, but with the second body 6 mounted to the second part 12 of the first body 2. According to a specific embodiment of the invention (for example in the first, second and fifth embodiments shown in FIGS. 5-8 and 20-21), the second body 6 further comprises a fifth access port 20 for a fluid and a sixth access port 21 for a fluid, the fifth 20 and sixth 21 access port being respectively directly connected, for fluid transport, to the third 7 and fourth 8 access port respectively by a fourth fluid path 22 and by a fifth fluid path 23.

Figure 9:
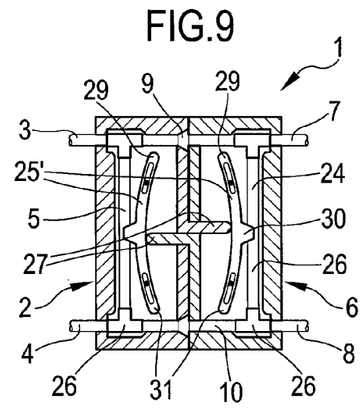
FIG. 9 shows a sectioned view of a third embodiment of a connector according to the present invention in a main operating position.
Figure 10:
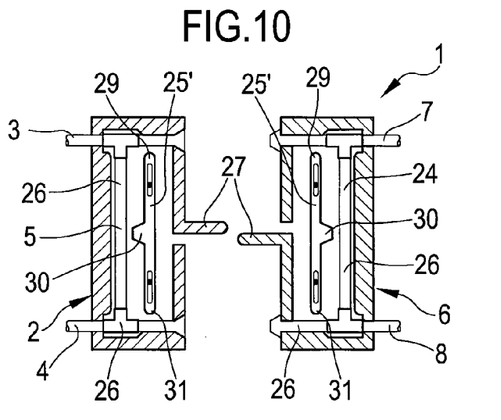
FIG. 10 shows the connector of FIG. 9 in an auxiliary operating position.
Figure 11:
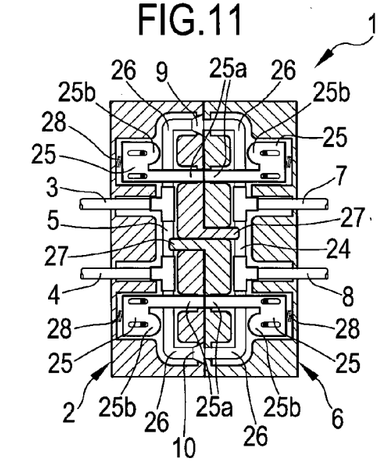
FIG. 11 shows a sectioned view of a fourth embodiment of a connector according to the present invention in a main operating position.
Figure 12:
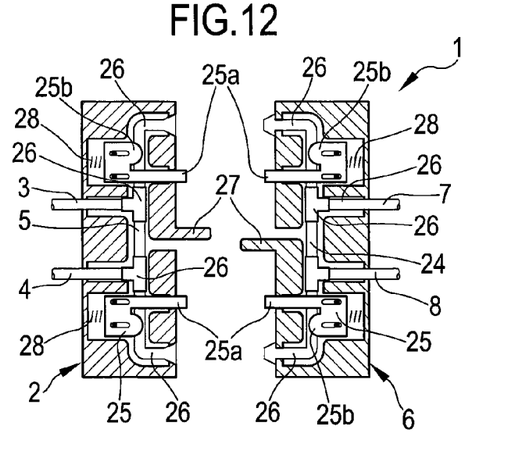
FIG. 12 shows the connector of FIG. 11 in an auxiliary operating position.

As shown for example in the third and fourth embodiments of FIGS. 9-12, the connector 1 can further comprise pushing elements 25 interrupting the second 9 and third 10 paths when the second body 6 is not mounted to the first body 2, the pushing elements 25 enabling the second 9 and third 10 paths when the second body 6 is mounted to the first body 2. According to the third and fourth embodiments of FIGS. 9-12, the connector 1 can further comprise tubes 26 for fluid transport inserted in the respective paths and at least a pushing element 25 adapted to selectively press the tubes 26 to prevent fluid passage and to interrupt corresponding paths. The connector 1 may comprise a plurality of pushing elements 25. The connector 1 may also comprise protrusions 27 of the first and/or second body 6 adapted to press at least one of the tubes 26 in the main operating position. The protrusions 27 may press the corresponding tubes 26 either directly, as shown in FIGS. 11-12, or indirectly, as shown in FIGS. 9-10. The pushing elements 25 may be movably mounted in the first 2 and/or second body 6 with elastic elements 28 to press at least one of the tubes 26 in order to interrupt fluid passage in the auxiliary operating position or in the main operating position (as shown in FIGS. 9-12). The pushing elements 25 are movably mounted in the respective body to shift between different operating position, in order to selectively enable or prevent fluid passage in at least one of the tubes 26 in a respective opposite operating position corresponding to the main or auxiliary operating position. In other words each pushing element 25 presses at least a corresponding tube 26 to prevent fluid passage in the same tube 26 in the main operating position, and does not press the same tube 26, thus allowing fluid passage, in the auxiliary operating position, or viceversa. As shown for example in the third embodiment of FIGS. 9-10, the pushing elements 25 may comprise at least a flexible elongated element 25' hingedly mounted in the first body 2 and another flexible elongated element 25' mounted in the second body 6, the elongated element 25' having at least a first protrusion 29 adapted to press a first corresponding tube 26 to prevent fluid passage and at least a second protrusion 30 adapted to enable fluid passage in a second corresponding tube 26, in the auxiliary position (FIG. 10), the first protrusion 29 being adapted to enable fluid passage in the first corresponding tube and the second protrusion 30 being adapted to press the second corresponding tube to prevent fluid passage, in the main position (FIG. 9). The flexible elongated element 25' has at least a third protrusion 31 adapted to press a third corresponding tube to prevent fluid passage in the auxiliary position, the third protrusion 31 being adapted to enable fluid passage in the third corresponding tube in the main position. As shown in FIGS. 9-10, the flexible elongated element 25' is disposed in the first body 2 and is moved in the main position by a respective protrusion 27 of the second body 6, and viceversa. In particular both flexible elongated elements 25' in the first body 2 and in the second body 6 are moved in the main position by a respective pushing element 27 of the respective opposed body. In particular, in the third embodiment (FIGS. 9-10), when the connector is in the main position of FIG. 9 the protrusion 27 of the first body pushes the flexible elongated element 25' in the second body and the protrusion 27 of the second body pushes the flexible elongated element 25' in the first body, so that the second protrusion 30 presses the tubes 26 corresponding to the first path 5 and the sixth path 24, thus preventing fluid circulation in such paths. At the same time the flexible elongated elements 25' are curved as shown in FIG. 9 so that the first and the third protrusion 29, 31 do not press the tubes corresponding to the second and third paths 9, 10, thus allowing fluid passage in such paths and connecting the main fluid line connected to the first body with the auxiliary fluid line connected with the second body. On the contrary, when the connector is in the auxiliary position of FIG. 10 the protrusion 27 of the first body is moved away from the flexible elongated element 25' in the second body and the protrusion 27 of the second body is moved away from the flexible elongated element 25' in the first body, so that the flexible elongated element 25' is no longer curved. In such position, the second protrusion 30 does not press the tubes 26 corresponding to the first path 5 and the sixth path 24, thus allowing fluid circulation in such paths. At the same time the first and the third protrusion 29, 31 press the tubes 26 corresponding to the second and third paths 9, 10, thus preventing fluid passage in such paths and connecting the two lines of the main fluid line connected to the first body between them and the two lines of the auxiliary fluid line connected with the second body between them. In this position the main fluid line and the auxiliary fluid line are separated and the auxiliary fluid line is bypassed.

In particular, in the fourth embodiment (FIGS. 11-12), when the connector is in the main position of FIG. 11 the protrusion 27 of the first body presses the tube 26 defining the sixth path 24 in the second body and the protrusion 27 of the second body presses the tube 26 defining the first path 5 in the first body, to preventing fluid circulation in such paths. At the same time in such position the pushing elements 25 are in a retracted position, with the elastic elements 28 compressed, due to contact between respective terminal portions 25a of the pushing elements 25, so that the same pushing elements 25 and respective pushing portion 25b are not in contact with respective tubes 26 defining the second and the third paths 9, 10, thus allowing fluid circulation in such paths.

Figure 18:
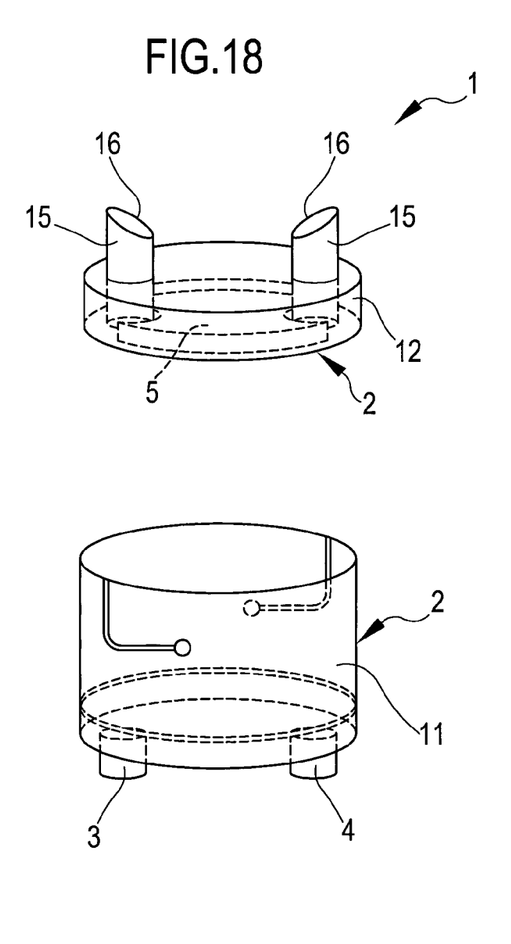
FIG. 18 is an exploded perspective view of the first part and of the second part of the first body of the connector of FIG. 13.
Figure 19:
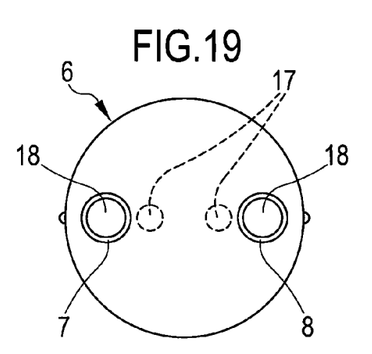
FIGS. 19 and 19a show respectively a view from above and a view from below of a second body of the connector of FIG. 13.
Figure 19A:
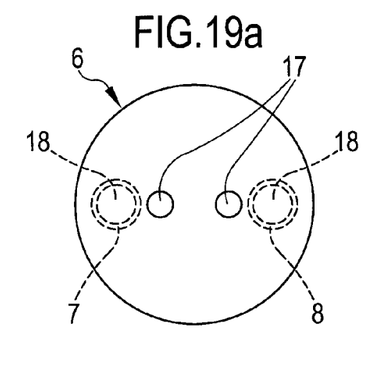

When the connector is in the auxiliary position of FIG. 12 the protrusions 27 of the first body and of the second body are away from the tubes 26 defining the sixth path 24 and the first path 5 in the first body, so that fluid flow is possible in such paths. At the same time in such position the pushing elements 25 are pushed in an advanced position by the elastic elements 28, so that the same pushing elements 25 and in particular their respective pushing portions 25b press respective tubes 26 defining the second and the third paths 9, 10, thus preventing fluid circulation in such paths. Accordingly in this position the two lines of the main fluid line connected to the first body are connected and the two lines of the auxiliary fluid line connected with the second body are reciprocally connected. In this position the main fluid line and the auxiliary fluid line are separated and the auxiliary fluid line is bypassed. According to a further variant of the invention, the connector 1 may also be realized with a single body comprising at least a first part and a second part movable with respect to the first part for defining said main and said auxiliary operating positions. An example of this variant is shown in FIG. 18, in which the connector 1 is defined by the sole first body 2 according to an aspect of the present invention. In this variant, the second part 12 of the first body 2 provides the function of the second body 6 and is rotatably movable with respect to the first part 11 to selectively enable the first path 5 (interrupting the second 9 and third 10 path) or the second 9 and the third 10 path (interrupting the first path 5). The second part 12 of the first body 2 may be directly connected to an auxiliary fluid line, without the need of the second body 6, as in the fifth embodiment.

Figure 20:
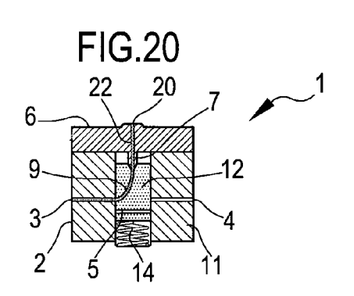
FIG. 20 shows a sectioned view of a sixth embodiment of a connector according to the present invention in a main operating position.
Figure 21:
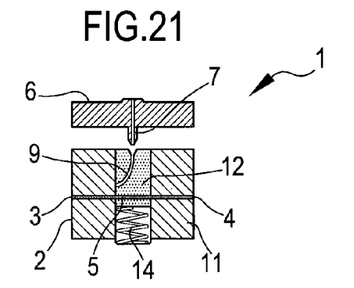
FIG. 21 shows the connector of FIG. 20 in an auxiliary operating position.
Figure 21A:
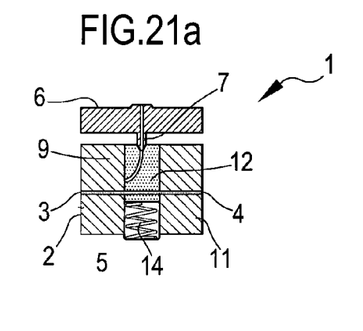
FIG. 21a shows a further intermediate position of the connector of FIG. 21, corresponding to the auxiliary operating position of a variant of the sixth embodiment.

In a sixth embodiment of the invention, shown in FIGS. 20, 21 and 21a, the connector 1 may comprise a first body 2 having a first access port 3 for a fluid, a second access port 4 for a fluid, and a first fluid path 5 extending in the first body 2 and directly connecting, for fluid transport, the first access port 3 and second access port 4, and at least a second body 6, mountable to the first body 2, having a third access port 7 for a fluid. The second body 6 is movable with respect to the first body 2 at least between a main operating position (FIG. 20) in which the first fluid path 5 is interrupted and in which a second fluid path 9 is defined and enabled, for fluid transport, from the first access port 3 to the third access port 7, and an auxiliary operating position (FIG. 21) in which the first fluid path 5 is enabled and in which the second fluid path 9 is interrupted. In this sixth embodiment, the second body 6 comprises only a third access port 7 that is selectively connectable to the first port of the first body 2 in the main operating position. In the sixth embodiment no fourth access port 8 and no third path is provided. This embodiment of the connector 1 is adapted for example to selectively connect a main fluid line having two lines with an auxiliary fluid line having only a single line. Also in this case the second body 6 may comprise a fifth access port 20 and a fourth fluid path 22 in the second body 6 connecting the third access port 7 with the fifth access port 20.

Figure 6:
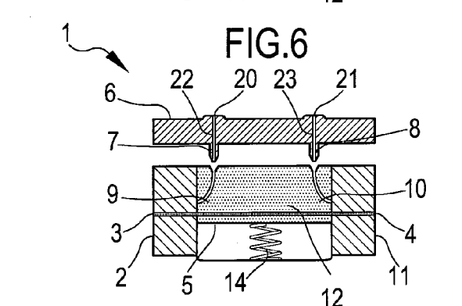
FIG. 6 shows the connector of FIG. 5 in an auxiliary operating position.
Figure 6A:
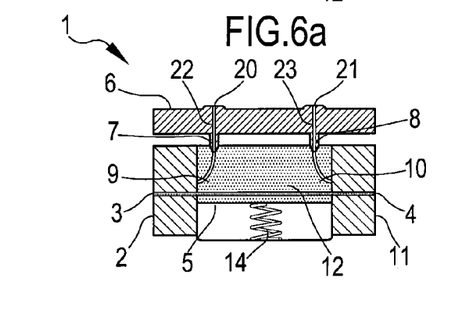
FIG. 6a shows a further intermediate position of the connector of FIG. 5, corresponding to the auxiliary operating position of a variant of the first embodiment.
Figure 7:
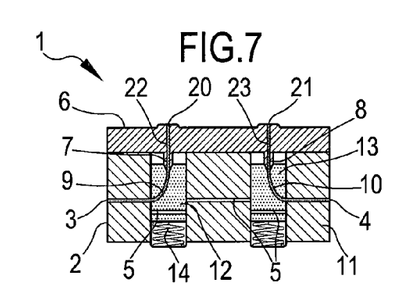
FIG. 7 shows a sectioned view of a second embodiment of a connector according to the present invention in a main operating position.
Figure 8:
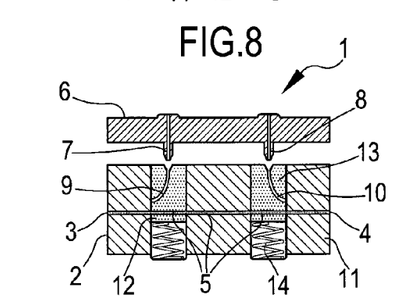
FIG. 8 shows the connector of FIG. 7 in an auxiliary operating position.
Figure 8A:
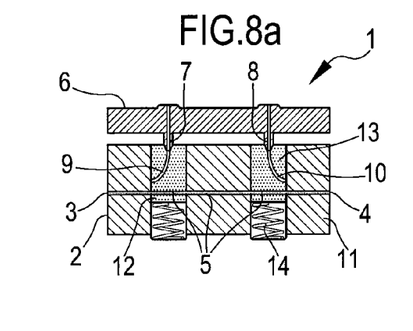
FIG. 8a shows a further intermediate position of the connector of FIG. 7, corresponding to the auxiliary operating position of a variant of the first embodiment.

In a variant of the first, second and sixth embodiments of the present invention, substantially illustrated respectively in FIGS. 5 and 6a, 7 and 8a and 20 and 21a, the connector 1 may comprise a second body 6 as in FIGS. 5-8 and 20-21, with the difference that in these variants the second body 6 is fixedly mounted to the first body 2 (and in particular to the second and/or third part of the first body 2). In such variants the auxiliary position corresponds to an intermediate position of the first and second embodiments, as shown in FIGS. 6a, 8a and 21a. In such position, the second and third part are in the same position of FIGS. 6, 8 and 21, but the second body 6 is still mounted to the second and third part as in FIGS. 5, 7 and 20. According to this variant the second body 6 may be made in one piece with the first body 2 or may be a part of the first body 2.

The invention further relates, in a further aspect, to a fluid transport line for a medical device comprising a main fluid line, an auxiliary fluid line and a connector 1 for a fluid transport line of a medical device comprising at least a body having a first access port 3 for a fluid, connected to a first access port of the main fluid line, a second access port 4 for a fluid, connected to a second access port of the main fluid line, a first fluid path 5 extending in the first body 2 and directly connecting, for fluid transport, the first access port 3 and second access port 4, a third access port 7 for a fluid, operatively connected to a first access port of the auxiliary fluid line, a fourth access port 8 for a fluid, operatively connected to a second access port of the auxiliary fluid line, a second fluid path 9 defined for fluid transport from the first access port 3 to the third access port 7, and a third fluid path defined for fluid transport from the second access port 4 to the fourth access port 8. According to this aspect of the invention the connector 1 defines a main operating position in which the first fluid path 5 is interrupted and in which the second fluid path 9 is enabled, for fluid transport, from the first access port 3 to the third access port 7, and in which the third fluid path is enabled, for fluid transport, from the second access port 4 to the fourth access port 8, and an auxiliary operating position in which the first fluid path 5 is enabled and in which the second and third fluid paths are interrupted, the auxiliary fluid line being bypassed by the connector 1 in the auxiliary operating position. The invention further relates to a method for automatically establishing and interrupting a fluid communication between a main fluid line and an auxiliary fluid line of a fluid transport line for a medical device, comprising the steps of selectively configuring a connector 1, having a first 3 and a second 4 access port for a fluid connected respectively to a first and a second access port of the main fluid line and a third 7 and a fourth 8 access port for a fluid operatively connected respectively to a first and a second access port of the auxiliary fluid line, between a main position in which a first fluid path 5, defined in the connector 1 for directly connecting, for fluid transport, the first access port 3 and second access port 4, is interrupted and in which a second fluid path 9 from the first access port 3 to the third access port 7 and a third fluid path from the second access port 4 to the fourth access port 8 are enabled, and an auxiliary position in which the first fluid path 5 is enabled and in which the second and third fluid paths are interrupted, the auxiliary fluid line being bypassed by the connector 1 in the auxiliary operating position. The invention further relates, in one of its aspects, to a method for automatically connecting and disconnecting a main fluid line and an auxiliary fluid line of a fluid transport line for a medical device, comprising the steps of selectively configuring a connector, having a first body with a first and a second access ports for a fluid connected respectively to a first and a second access port of the main fluid line and a second body with a third and a fourth access ports for a fluid operatively connected respectively to a first and a second access ports of the auxiliary fluid line, between a main position in which the second body is mounted to the first body and in which a first fluid path, defined in the connector for directly connecting, for fluid transport, the first access port and second access port, is interrupted and in which a second fluid path from the first access port to the third access port and a third fluid path from the second access port to the fourth access port are enabled, and an auxiliary position in which in which the second body is separated from the first body, the first fluid path is enabled and in which the second and third fluid paths are interrupted, the auxiliary fluid line being bypassed and separated from the main fluid line in the auxiliary operating position. According to the variant of the first, second and sixth embodiments above described (FIGS. 6a, 8a and 21a), the methods above described may also be implemented with a connector having a second body with a third access port and without a fourth access port, and consequently connected to an auxiliary fluid line having a single fluid line.

ADVANTAGES OF THE INVENTION

The present invention affords at least one or more of the following advantages:
- a connector and a method according to one aspect of the invention overcome some of the limits of the known art;
- a connector and a method according to one aspect of the invention allow to selectively exclude a part of a fluid flow circuit from the remaining part of the circuit in a simple and quick manner;
- a connector according to one aspect of the invention has a simple and robust structure.
- a connector according to one aspect of the invention can be easily and quickly actuated to bypass a certain part of the circuit;
- a connector according to one aspect of the invention is cheap and reliable.
- a connector and a method according to one aspect of the invention can be simply realized and are not expensive.

LIST OF REFERENCE NUMBERS connector 1
first body 2
first access port 3
second access port 4
first fluid path 5
second body 6
third access port 7
fourth access port 8
second fluid path 9
third fluid path 10
first part 11
second part 12
third part 13
elastic element 14
protruding portions 15
upper edge 16
channels 17
cursors 18
elastic elements 19
fifth access port 20
sixth access port 21
fourth fluid path 22
fifth fluid path 23
sixth fluid path 24
pushing elements 25
terminal portion 25a
pushing portion 25b
flexible elongated element 25'
tubes 26
protrusions 27
elastic elements 28
first protrusion 29
second protrusion 30
third protrusion 31
fluid flow circuit 100
hydraulic circuit 101
supply channel 102
source 103
inlet branch 104
blood treatment unit 105
discharge channel 106
evacuation zone 107
blood circuit 108
arterial line 109
vascular access 110
venous line 111
blood chamber 112
second chamber 113
membrane 114
air separators 115
safety valve 116
pump 117
blood pressure sensor 118
device for administering an anticoagulant 119
pressure sensor 120
air bubble sensor 121
pump 122
pressure sensor 123
drainage pump 124
blood leak detector 125
ultrafilters 126
main fluid line 127
auxiliary fluid line 128

The invention claimed is:

1. A connector of a fluid transport line of a medical device comprising:
   a first body including a first access port for a fluid, a second access port for a fluid, and a first fluid path extending through said first body and directly connecting, for fluid transport, said first access port to said second access port;
   at least a second body, mountable to said first body, having at least a third access port for a fluid, said second body is movable with respect to said first body at least between:
   a main operating position in which said first fluid path is interrupted and in which a second fluid path is defined and enabled, for transport of a fluid, from said first access port to said third access port, and
   an auxiliary operating position in which said first fluid path is enabled and in which said second fluid path is interrupted, and wherein the main operating position and the auxiliary operating position are defined by relative positions of the first body and the second body; and
   wherein the first body includes a first part, and a second part in through which a portion of said first fluid path and a portion of said second fluid path are defined, and wherein said second part is (i) in a first position with respect to said first part in the auxiliary operating position and (ii) in a second position with respect to said first part in the main operating position.

2. The connector according to claim 1, wherein said second body has at least a fourth access port for a fluid and wherein in said main operating position a third fluid path is defined and enabled, for transport of a fluid, from said second access port to said fourth access port, said third fluid path being interrupted in said auxiliary operating position.

3. The connector according to claim 2, wherein said second body comprises a sixth fluid path for directly connecting said third access port to said fourth access port for transport of a fluid, said sixth fluid path being enabled in said auxiliary position and being interrupted in said main position.

4. The connector according to claim 2, further comprising pushing elements interrupting said second and third paths when said second body is not mounted to said first body, said pushing elements enabling said second and third paths when said second body is mounted to said first body.

5. The connector according to claim 2, wherein the first body further comprises a third part in which a portion of the first path and a portion of the third path are defined, the third part being also movable with respect to the first part between a first position, corresponding to the auxiliary operating position, in which the first path is enabled, and a second position, corresponding to the main operating position, in which the first path is interrupted and the third path is enabled.

6. The connector according to claim 5, wherein the second body is mounted to the second part and/or the third part of the first body in the main position and is detached from the second part and/or the third part in the auxiliary position.

7. The connector according to claim 2, wherein the first, second and/or third path are respectively enabled by aligning the portions of the first, second or third path defined in the second part and/or third part with corresponding portions of fluid path defined in the first part of the first body.

8. The connector according to claim 1, wherein said second body is removably mounted to said first body and/or in which said second body is detached from said first body in said auxiliary operating position and is mounted to said first body in said main position.

9. The connector according to claim 1, further comprising tubes for transport of a fluid inserted in or defining said paths and at least a pushing element adapted to selectively press said tubes to prevent fluid passage and to interrupt corresponding paths.

10. The connector according to claim 1, wherein the second body is in contact with the first body either in the main operating position or in the auxiliary operating position.

11. The connector according to claim 1, comprising a plurality of pushing elements presenting protrusions of the first and/or second body configured to press at least one tube in the main operating position.

12. The connector according to claim 11, wherein the pushing elements are movably mounted in the first and/or second body through elastic elements, to push said at least one tube to interrupt fluid passage in the auxiliary operating position or in the main operating position, the pushing elements being movable to enable fluid passage in the said at least one tube in a respective opposite operating position corresponding to the main or auxiliary operating position.

13. The connector according to claim 11, wherein the pushing elements comprise a flexible elongated element hingedly mounted in the first body and/or in the second body, the elongated element having at least a first protrusion configured to press a first corresponding tube to prevent fluid passage and at least a second protrusion configured to enable fluid passage in a second corresponding tube, in the auxiliary position, the first protrusion being configured to enable fluid passage in the first corresponding tube and the second protrusion being configured to press the second corresponding tube to prevent fluid passage, in the main position.

14. The connector according to claim 13, wherein the flexible elongated element has at least a third protrusion adapted to press a third corresponding tube to prevent fluid passage in the auxiliary position, the third protrusion being adapted to enable fluid passage in the third corresponding tube in the main position, the flexible elongated element being disposed in the first body and moved in the main position by a respective pushing element of the second body, and/or vice versa.

15. A fluid transport line for a medical device comprising:
a main fluid line;
an auxiliary fluid line;
a connector including
  a first body including
    a first access port for a fluid connected to a first access port of said main fluid line;
    a second access port for a fluid connected to a second access port of said main fluid line; and
    a first fluid path extending through said first body and directly connecting, for fluid transport, said first access port to said second access port;
  a second body including
    a third access port for a fluid operatively connected to a first access port of said auxiliary fluid line;
    a fourth access port for a fluid, operatively connected to a second access port of said auxiliary fluid line; and
    a second fluid path defined for fluid transport from said first access port to said third access port, and
  a third fluid path defined for fluid transport from said second access port to said fourth access port, said connector defining
  a main operating position in which said first fluid path is interrupted and in which said second fluid path is enabled, for fluid transport, from said first access port to said third access port, and in which said third fluid path is enabled, for fluid transport, from said second access port to said fourth access port, and
  an auxiliary operating position in which said first fluid path is enabled and in which said second and third fluid paths are interrupted, said auxiliary fluid line being bypassed by said connector in said auxiliary operating position, wherein the main operating position and the auxiliary operating position are defined by relative positions of the first body and the second body; and
  wherein the first body includes a first part, and a second part in through which a portion of said first fluid path and a portion of said second fluid path are defined, and wherein said second part is (i) in a first position relative to said first part in the auxiliary operating position and (ii) in a second position relative to said first part in the main operating position.

16. A method for automatically establishing and interrupting a fluid communication between a main fluid line and an auxiliary fluid line of a fluid transport line for a medical device via a connector, the connector including (i) a first body including first and second access ports for a fluid connected respectively to first and second access ports of said main fluid line, and (ii) a second body including third and fourth access ports for a fluid operatively connected respectively to first and second access ports of said auxiliary fluid line, wherein the first body of the connector further includes a first part, and a second part through which a portion of a first fluid path and a portion of a second fluid path are defined, the method comprising:
selectively configuring the connector between (a) a main position in which the first fluid path, defined in the connector for directly connecting, for fluid transport, said first access port to said second access port, is interrupted and in which the second fluid path from said first access port to said third access port and the third fluid path from said second access port to said fourth access port are enabled, and (b) an auxiliary position in which said first fluid path is enabled and in which said second and third fluid paths are interrupted, said auxiliary fluid line being bypassed by said connector in said auxiliary operating position; and further selectively configuring the connector so that (c) the second part is movable with respect to said first part between the auxiliary position and the main position.

17. A medical fluid passage device comprising:
a first body including a first access port, a second access port, and a first fluid passage extending between said first access port and second access port, and
a second body mountable to said first body and including a third access port, wherein said second body has
  a first operating position relative to the first body in which said second body obstructs the first fluid passage and opens a second fluid passage between the first access port and the third access port, and
  a second operating position relative to the first body in which said second body obstructs the second fluid passage and opens the first fluid passage; and
wherein the first body includes a first part, and a second part through which a portion of said first fluid passage and at least a portion of said second fluid passage are defined, and wherein said second part is (i) in a first position relative to said first part in the second operating position, in which said first fluid passage is opened and (ii) in a second position relative to the first part in the first operating position, in which said first fluid passage is obstructed and said second fluid passage is opened.

* * * * *